United States Patent [19]

Wellstood et al.

[11] Patent Number: 5,894,220
[45] Date of Patent: Apr. 13, 1999

[54] APPARATUS FOR MICROSCOPIC IMAGING OF ELECTRICAL AND MAGNETIC PROPERTIES OF ROOM-TEMPERATURE OBJECTS

[75] Inventors: Frederick Charles Wellstood, Lanham; Yonggyu Gim, College Park, both of Md.; Randall Christopher Black, San Diego, Calif.; Steven M. Green, Greenbelt, Md.

[73] Assignee: University of Maryland, College Park, Md.

[21] Appl. No.: 08/600,168

[22] Filed: Feb. 12, 1996

[51] Int. Cl.$^6$ ............... G01R 33/035; G01R 31/00; G01N 27/72; G01J 5/00
[52] U.S. Cl. ............... 324/248; 250/330; 250/338.1; 324/226; 324/235; 324/240; 324/261; 324/262; 324/457; 324/750; 382/147; 505/160; 505/842; 505/846; 505/849
[58] Field of Search ............... 324/201, 226, 324/235, 240–242, 248, 249, 251, 252, 260–262, 95, 96, 451, 452, 457, 750; 250/330, 336.2, 338.1, 352, 372; 382/145, 147; 505/842, 843, 845–847, 160–162; 235/449

[56] References Cited

U.S. PATENT DOCUMENTS

| | | | |
|---|---|---|---|
| 4,861,990 | 8/1989 | Coley | 324/201 X |
| 4,862,002 | 8/1989 | Wang et al. | 250/352 |
| 4,982,158 | 1/1991 | Nakata et al. | 324/248 X |
| 5,004,724 | 4/1991 | De | 324/248 X |
| 5,059,903 | 10/1991 | Otaka et al. | 324/248 X |
| 5,293,119 | 3/1994 | Podney | 324/248 X |
| 5,315,247 | 5/1994 | Kaiser et al. | 324/244 |
| 5,355,085 | 10/1994 | Igarashi et al. | 324/248 |
| 5,372,132 | 12/1994 | McClain | 324/248 X |
| 5,408,178 | 4/1995 | Wikswo, Jr. et al. | 324/201 |
| 5,420,100 | 5/1995 | Vittoria et al. | 324/248 X |
| 5,437,276 | 8/1995 | Takada | 324/248 X |
| 5,438,265 | 8/1995 | Eslambolchi et al. | |
| 5,442,289 | 8/1995 | Dilrio et al. | 324/248 |
| 5,469,057 | 11/1995 | Robinson | 324/248 |
| 5,471,985 | 12/1995 | Warden | 324/248 X |
| 5,488,295 | 1/1996 | Seppä | 324/248 |
| 5,491,411 | 2/1996 | Wellstood et al. | 324/248 |
| 5,600,143 | 2/1997 | Roberts et al. | 250/332 X |

FOREIGN PATENT DOCUMENTS 5-190916  7/1993  Japan .................... 324/248

OTHER PUBLICATIONS

Buchanan et al; "Micrcosquid: A Close–Spaced Four Channel Magnetometer", Advances in Biomagnetism, Plenum, New York: S.J. Williamson, 1989, pp. 677–679.

Primary Examiner—Gerard R. Strecker
Attorney, Agent, or Firm—Nikaido, Marmelstein, Murray & Oram LLP

[57] ABSTRACT

A cryogenic apparatus for microscopy of physical properties of an object including a thin, stiff, transparent substrate or window within the outer wall of the vacuum space of a dewar and a cryogenic sensor within the vacuum space and spaced very close distances to the window. This construction allows for positioning a sample for measurement outside of the vacuum space, at room temperature or higher and for microscopy of physical properties of the sample by monitoring the output from the cryogenic sensor as it is scanned along the surface of the sample.

31 Claims, 10 Drawing Sheets

APPARATUS FOR MICROSCOPIC IMAGING OF ELECTRICAL AND MAGNETIC PROPERTIES OF ROOM-TEMPERATURE OBJECTS

FIELD OF THE INVENTION

The present invention relates to a device, which includes a cryogenic sensor housed within a vacuum space, for microscopy of physical properties of a room-temperature object located outside the vacuum space.

BACKGROUND OF THE INVENTION

In recent years, with the advent of microelectronics circuitry and related advances in electrical engineering, many industries have found a greater need to non-invasively measure the electrical and magnetic properties of materials and devices. The process of magnetic imaging at high spatial resolution and high sensitivity has been impractical, while low sensitivity or low spatial measurements have been unable to resolve crucial electrical properties.

In the field of semiconductors/microelectronics testing, there is a need to measure the current flow and image the data relating to the operation of semiconductor/microelectronic devices and their related current paths.

With the advent of magnetic resonance imaging in the field of biology, many new discoveries have been made regarding biological and biochemical subjects. Unfortunately, none of the current technologies applied in this field provide a very sensitive reading in the picotesla range at low frequencies, or provide good spatial resolution at high frequencies.

A number of techniques have been developed to image magnetic fields at length scales of a few μm or relatively smaller. These include decoration techniques, magnetoresistive or Hall probe sensors, magneto-optic thin films, magnetic force microscopy, and electron beam interferometry. These techniques have provided limited success and are not practical for high resolution and high sensitivity imaging of fields and flux lines.

Additionally, a number of susceptometers and magnetometers have been proposed using Superconducting Quantum Interference Devices, or SQUIDS. Though previous SQUID systems have been developed to provide high magnetic field resolution, they are impractical to implement in a microscope imaging device. The prior art magnetic imaging devices using SQUIDS have had spatial resolution on the scale of a mm or larger which is too crude for microscopically resolving images. These devices may also require placing samples in a vacuum. Of course, many samples such as liquids and biological specimens cannot tolerate a vacuum. Thus it is not practical to measure sources of biomagnetism which are currently the focus of much of the existing low-spatial-resolution SQUID imaging work.

U.S. patent application Ser. No. 08/061,102, now U.S. Pat. No. 5,491,411, entitled "Method and Apparatus for Imaging Microscopic Spatial Variations in Small Currents and Magnetic Fields," by Wellstood et al., herein incorporated in its entirety by reference, discloses one such apparatus capable of providing all of the above discussed measurements with enhanced spatial resolution and magnetic field sensitivity. However, the device still requires placing a sample within a dewar, which may result in the unwanted destruction of the sample when it is exposed to the cryogenic liquid or vacuum. Even if the sample could tolerate the vacuum environment or cryogenic environment, it is time consuming and cumbersome to introduce a sample into a vacuum space for imaging. Another shortcoming is the limited size of the samples that can be imaged.

SUMMARY OF THE INVENTION

Therefore, an object of the present invention is to conveniently measure the physical properties, such as the electrical and magnetic properties, of a sample.

Another object of the invention is to measure microscopic physical properties of a sample without destroying the sample.

Another object of the invention is to allow for magnetic and electrical imaging of objects which are bigger than objects now measured by conventional devices.

Another object of the invention is to allow the use of cryogenic sensors for obtaining microscopically spatially resolved images of physical objects of room temperature samples.

Another object of the invention is to generate microscopic spatially resolved images of the magnetic and electrical properties of samples at room temperature.

These and other objects of the invention are obtained by including a thin, stiff, transparent substrate or window within the outer wall of the vacuum space of a dewar and a cryogenic sensor within the vacuum space and spaced very close distances to the window. This construction allows for positioning a sample for measurement outside of the vacuum space, at room temperature or higher and for microscopy of physical properties of the sample by monitoring the output from the cryogenic sensor as it is scanned along the surface of the sample.

BRIEF DESCRIPTION OF SEVERAL VIEWS OF THE DRAWINGS

FIG. 14b is a side view of 14a.

DETAILED DESCRIPTION OF THE INVENTION

In a preferred embodiment of the invention, the apparatus of the invention is composed of a modified dewar, a cryogenic sensor, a stage, and a computer and its associated software and electronic connections to the stage to maneuver the stage.

Figure 1A:
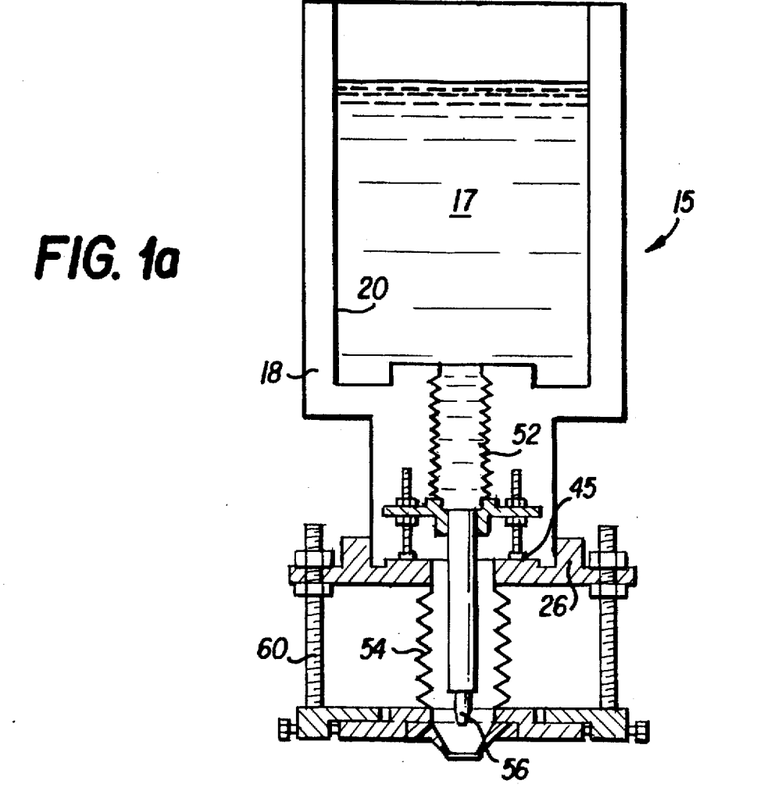
FIG. 1a is a schematic diagram of the device of invention.
Figure 1B:
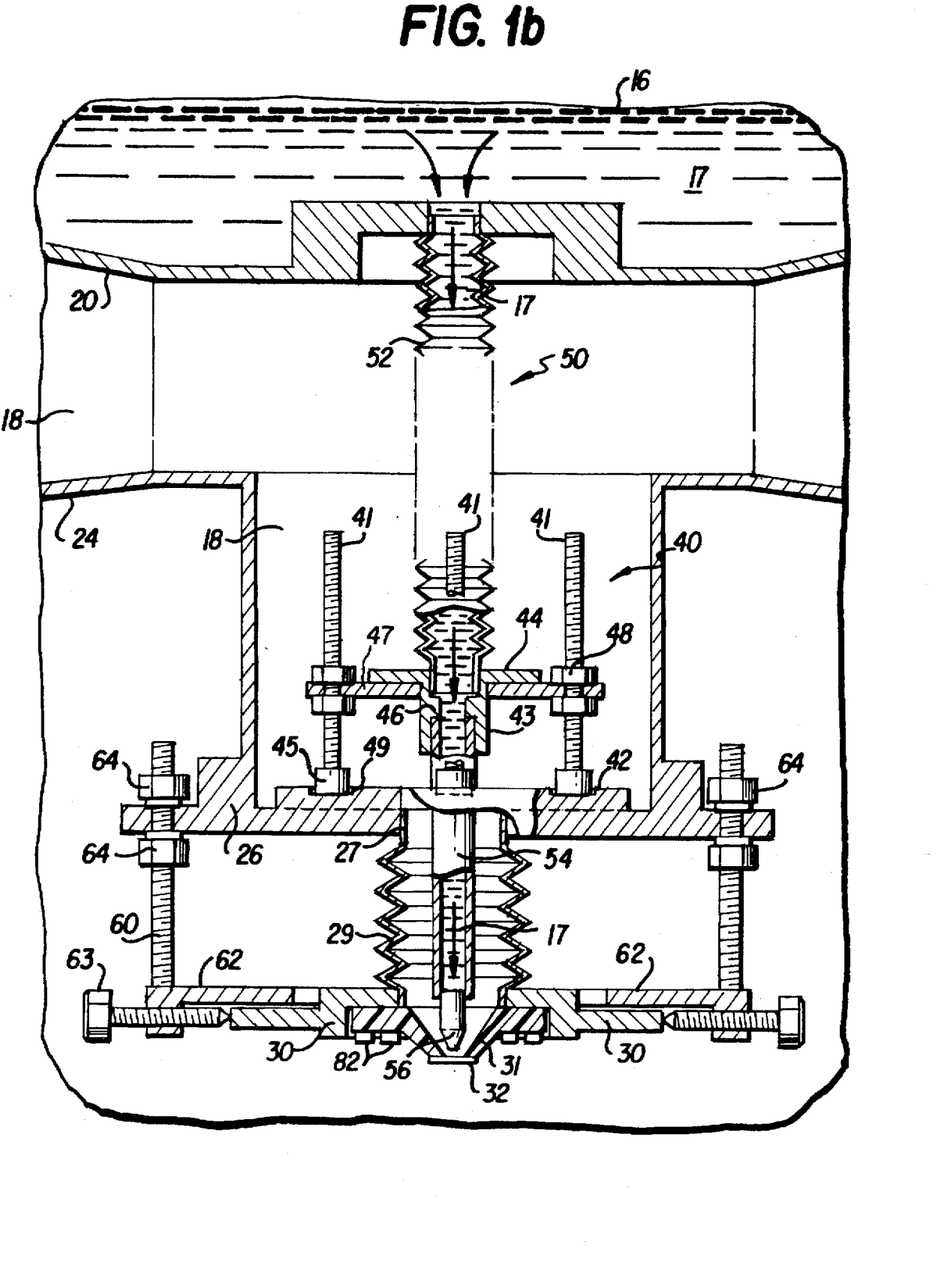
FIG. 1b is a fragmentary schematic view of features of the device of the invention, including a cryogenic sensor within the vacuum space of a dewar and a thin transparent window in the outer wall of the dewar.

A major portion of the device of the invention shown in FIGS. 1a and 1b includes modified dewar assembly 15 having a vacuum space maintained at about $10^{-5}$ Torr containing a cryogenic sensor and a cryogenic space containing about twenty liters of a cryogenic liquid.

In particular, dewar 15 shown in FIG. 1b is a modified commercial stainless steel liquid nitrogen dewar having a cryogen-containing portion 16 for receiving and holding liquid nitrogen 17, and a vacuum space 18 which thermally insulates the cryogen from room temperature. The modification consists of removing a portion of the "superinsulation" 20 of the commercial dewar and replacing the removed portion with an assembly 22 that includes outer walls or housing 24, which defines the outer boundary of the vacuum space of the dewar and for maintaining a vacuum. Housing 24 is welded to the original dewar. Housing 24 includes: an annular plate 26, having a circular opening 27 in its center, and located radially outwardly from central opening 27, on top of the annular plate, is circular channel 49; a transparent and thin substrate or window 28 located below and spaced apart from annular plate 26; metallic bellows 29, connecting structures 30, plastic flange (ULTEM, a nylon composition) 31 and glass slide window support 32 having an annular opening, all of which are structures defining the distance between annular plate 26 and window 28 (see FIG. 2).

The modification to dewar 15 also includes bracing assembly 40. Bracing assembly 40 is composed of three footers 41 arranged in a triangular configuration relative to each other, grommet 43 having an annular exterior flange 44 and an annular interior flange 46. The bottom ends of footers 41 are bolted on ring 45 seated in channel 49. Good mechanical contact between ring 45 and channel 49 is achieved by tying nylon bristles 42 around ring 45. This construction also ensures a weak thermal contact between the bracing assembly 40 generally maintained at 77° K and the room temperature plate 26 and window 28. Bracing disk or plate 47 located approximately one inch from plate 26 and parallel thereto has three holes 48 for receiving complementarily threaded footers held in place by nuts. Plate 47 is connected to the grommet by bolts to exterior flange 44.

The annular plate 26 as shown in FIG. 1b is also connected via threaded rods 60 to horizontal adjustment annular disk 62 with adjustment screws 63 positioned as shown. Vertical adjustment nuts 64 on rods 60 are positioned on each side of the annular plate and allow fine movement of window 28 with respect to SQUID 72.

The final modification to dewar 15 is cryogen delivery system 50 that includes stainless steel bellows 52, copper or brass tube 54, and thermally conducting substrate, preferably a sapphire rod 56. Stainless steel bellows 52 is sealed to and is in open communication, at a first end, with the cryogen-containing portion 16 of dewar 15. The second end of stainless steel bellows 52 is located in the vacuum space 18 and is in open communication with the annular inner space of the grommet 43. This second end of bellows 52 is seated on the top of interior flange 46 of the grommet. The purpose of this assembly is to cool the cryogenic sensor 70 and SQUID chip 72 (see FIG. 4c) to operating temperature while simultaneously holding them rigid with respect to the dewar and minimizing the effects of thermal contraction in the walls of dewar 15.

The first end of copper tube 54 is received in the bottom inner annular space of the grommet 43 and is seated and soldered on the bottom of interior flange 46 of the grommet and is in open communication with the annular space of the grommet. Tube 54 extends through vacuum space 18, and through opening 27 in annular plate 26. Located in the second end of tube 54 and fastened thereto with epoxy is one end of thermally conducting substrate 56 which is sapphire and rod-shaped. The second end of the rod-shaped substrate is fabricated with a blunt end point, to which is fastened chip 72 positioned within an adjustable distance and preferably within a few microns of window 28 the adjustment being provided by adjustment rod 60 and nuts 64. Specifically, the distance between sensor 70 and window 28 may be as great as 2-3 mm or there may be no distance between them when they are touching. This construction allows for maintenance of sensor temperature at 77° K while allowing for minute separations between the sensor and a room-temperature sample.

It is pointed out that at room temperature the stainless steel bellows 52 exerts a force on bracing assembly 40, holding it in good mechanical contact with annular ring 26. When the cryogenic liquid is introduced into the dewar so that the liquid passes through the stainless steel bellows 52 and the copper tube 54, dewar 15 will contract but the position of the point will be unchanged because bellows 52 will stretch. Tube 54 will also contract, but this movement is countered by the contraction of footers 41, which are in heat exchange contact with the cryogenic liquid through connection to plate 47 and copper grommet 43.

Of course, by constructing the footers of zinc and other metal parts of copper, brass and stainless steel as described or of other metals, and noting the physical expansion and contraction properties of such metals, thermal expansion and contraction of the parts can be anticipated such that the sapphire rod and cryogenic sensor do not move at all or move very little upon cooling or warming of the dewar. Correction of any such movement of the sapphire rod in the vertical direction can be accomplished by hand, by adjusting vertical adjustment nuts 64. Lower bellows 29 allows for such movement.

As indicated above, an improvement of the invention is the microscopic imaging of a room temperature object or sample located outside of the dewar with the ability to bring a cryogenic sensor within microns of the sample. To this end, the apparatus of the invention includes a scanning sample stage 90 (see FIG. 5) that is located outside the dewar which is a considerable simplification as compared to stages used in previous scanning SQUID microscopes. Such stages required precision engineering for thermal contract and careful design to overcome the lack of lubrication in cryogenic temperatures. Notwithstanding the temperature advantage, the requirements of the scanning stage used in the present invention are similar, for instance, to the stage disclosed in U.S. Ser. No. 08/061,102. In particular, the mechanism should have a 1 µm positioning accuracy; it should ideally be non-magnetic and non-metallic, and preferably the stage is motorized. In addition to the capability of moving in the x-y directions, stage 90 should also have capability of moving in the vertical direction in order to raise or lower the sample to the window of the invention and allow for easy insertion of samples. A vertical translation stage similar to the height adjustment mechanism used in a standard optical microscope can be used. The vertical translation stage can be mounted above or below the x-y scanning stage allowing distances of between 2 inches to µm lengths between a sample 91 (see FIG. 2) on the stage and window 28. In fact, the sample can be touching the window. The vertical translation part of stage 90 used in the present invention is commercially available and was purchased from Edmund Scientific Co. as part no. J3608. Although this is a metallic stage, a one-inch thick plexiglass stand-off or spacer is placed between a sample and stage 90 to prevent undesirable magnetic interference from the metal of the stage to the cryogenic sensor. Also, limited success in removing residual magnetization was achieved by degaussing the steel components in stage 90 using a bulk magnetic tape eraser.

Figure 5:
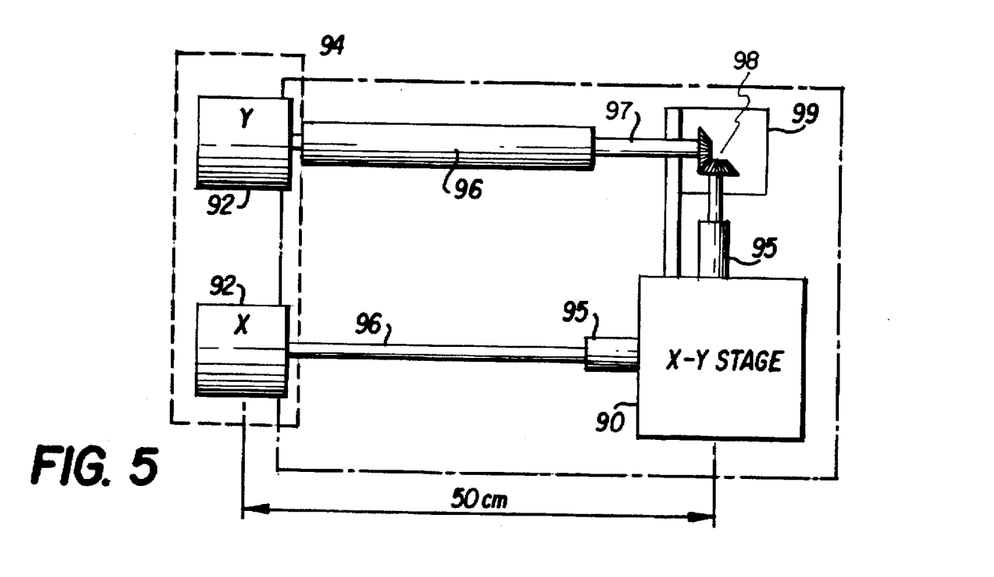
FIG. 5 shows a top view of the stage and mechanism for moving the stage upon which the sample is placed for measurement.

The stage 90 and stepper motors 92 for driving the x and y axes of stage 90 are shown in FIG. 5.

To automate the scanning process, motors 92 are used to drive the scanning x-y stage. Unfortunately, undesirable magnetic fields produced by the motors can easily couple into the SQUID because there is virtually no magnetic shielding between the SQUID and motors 92. Therefore, it is important to mount the motors as far as possible from the SQUID (about 50 cm) and to envelope them in eddy-current magnetic shields such as 1.5 mm-thick aluminum box 94 as shown in phantom in FIG. 5, which provides magnetic shielding above about 1 kHz. Motors 92 are mechanically coupled to micrometers 95 and single shafts 96 (x-axis) and a spline 97 coupled to and a right-angle coupler 98 (y-axis) through a 10:1 reduction right angle gear box 99. This design allows one to easily change the separation between motors and stage by simply extending shafts 96. Although magnetically noisy, stepper motors and microstepping drives are used because they provide excellent positioning accuracy.

Figures 6, 15:
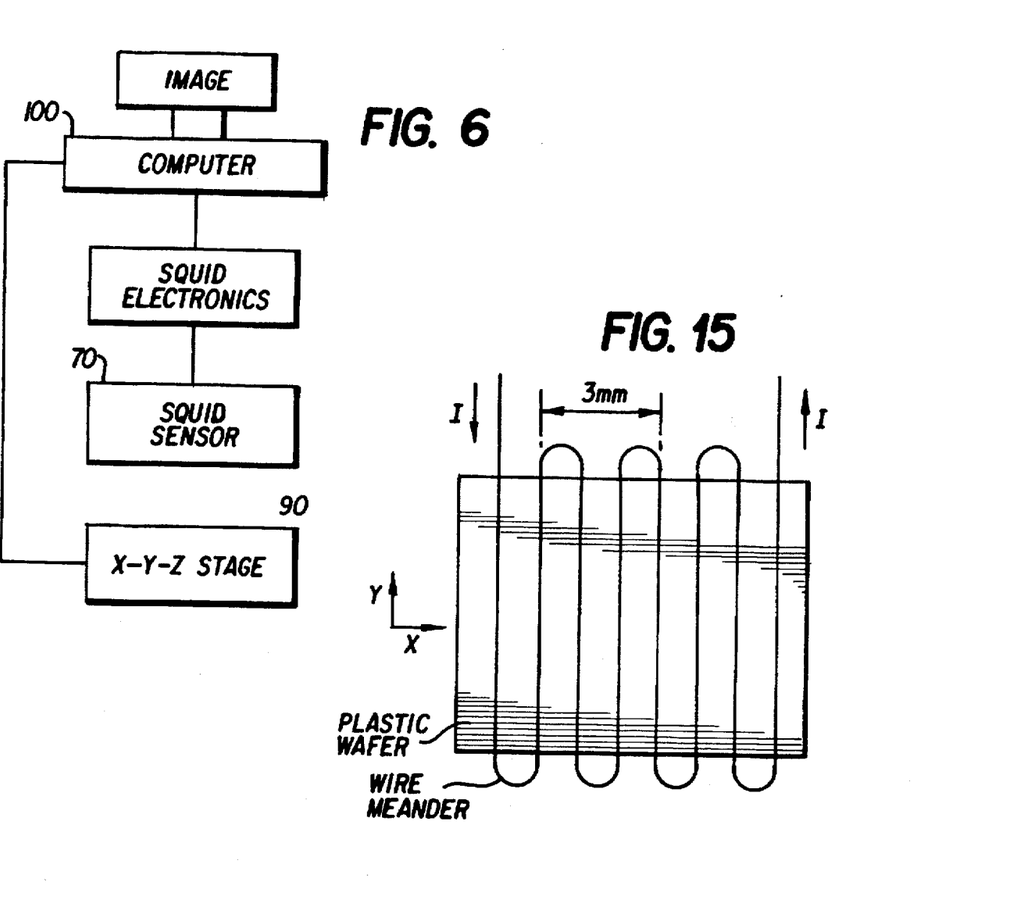
FIG. 6 is a schematic representation of a preferred embodiment of the invention.
FIG. 15 is a photograph of wire bent into a meander pattern carrying an alternating current at 400 MHz.

The CPU with controlling software and peripherals for operating the motor, is shown in the block diagram of FIG. 6.

In greater detail, thermally conducting substrate 56, in a preferred embodiment, is a sapphire rod, one-inch long with a 0.25 inch diameter. Sapphire has a large thermal conductivity at low temperatures (at 77° K, about 10 W cm$^{-1}$deg$^{-1}$). Substrate 56 supports the cryogenic sensor 70 which, in a preferred embodiment is a SQUID chip 72 (see FIGS. 3a and 3b).

Figure 3A:
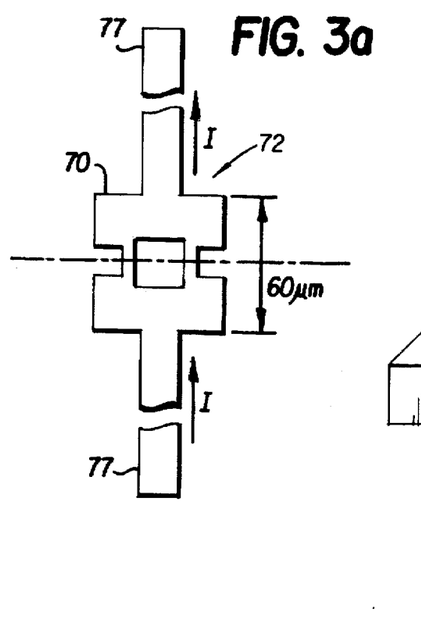
FIG. 3a and 3b are schematic views of a SQUID.
Figure 3B:
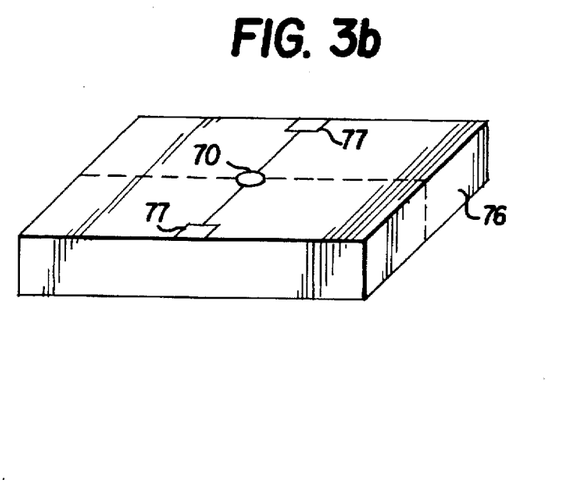

SQUID chip 72 consists of a single 200 nm-thick layer of YBa$_2$Cu$_3$O$_7$ as known in the art, is deposited on a 500 µm thick, 10 mm by 10 mm SrTiO$_3$ 24° bicrystal substrate using pulsed layer deposition. See, for instance, R. Gross et al., "Low Noise YBa$_2$Cu$_3$O$_{7-\delta}$ Grain Boundary Junction dc SQUID," Appl. Phys. Lett. Vol 57, p. 727 (1990), herein incorporated by reference. The SQUID sensor 70, as shown in FIG. 3a, has a square washer shape with an inner hole size of about 20 µm and an outer size of 60 µm. This geometry gives a measured effective magnetic pick up area of approximately 1.33×10$^{-9}$m$^2$. Gold contacts 77 are deposited onto the chip as shown.

Figure 4A:
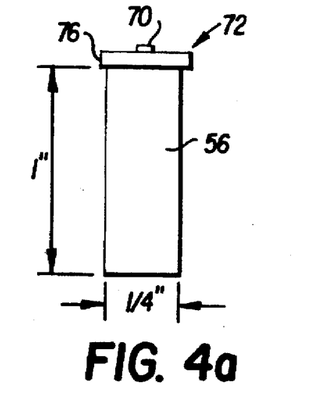
FIGS. 4a through 4c show, in sequence, stages in the manufacture of a SQUID and sapphire point cold-finger, which is an example of the cryogenic measuring device used in the present invention.
Figure 4B:
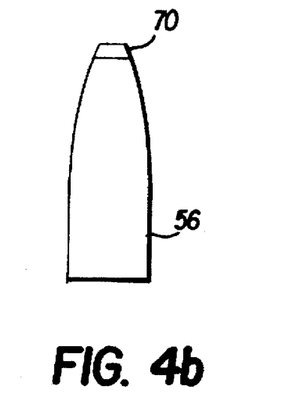
Figure 4C:
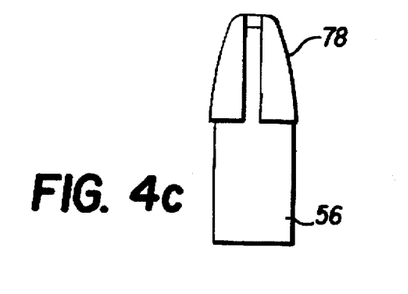

Since the SQUID is small it is difficult to handle. The small chip requires a special mounting procedure which is shown in FIGS. 4a through 4c. Once a working SQUID is obtained on a SrTiO$_3$ chip, the chip side of the sensor is epoxied to an end of the one-inch long, 0.25 inch diameter sapphire rod using STYCAST 2850 FT epoxy, creating the structure shown in FIG. 4a. To ensure an adequate bond the mating surfaces of these structures were also etched. The SrTiO$_3$ epoxy and sapphire are then ground away using a diamond-grit polishing wheel leaving a 800 µm-diameter tip at the end (see FIG. 4b). Additional epoxy may be used to coat exposed edges. The tip consists of the disk of SrTiO$_3$ containing at least one SQUID and gold contacts. To make the electrical contact to the surface of this chip, three silver contacts 78 about 200 nm thick are deposited over the edges of the chip and down the side of the sapphire rod (see FIG. 4c).

As is known in the art, SQUIDS are usually operated in a negative feedback loop or flux-locked loop.

Figure 2:
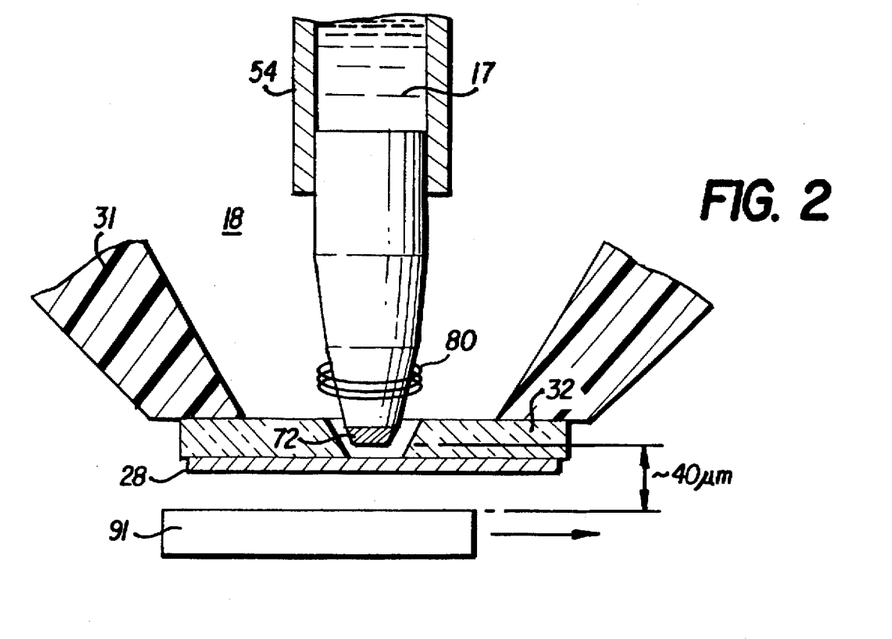
FIG. 2 is a magnified plan view of the encircled portion of the device of FIG. 1b.

To couple magnetic flux into the SQUID for maintaining a flux-locked loop, or for applying the read-out flux required for other imaging schemes, a simple three-turn coil 80 was wrapped around the sapphire rod as shown in FIG. 2. A mutual inductance of approximately 0.24 pH between the SQUID loop and the coil was measured. It is determined that mutual inductance can be increased by fabricating an electronics squid output feedblock coil 80 directly on the SQUID chip using photolithographic printing techniques known in the art.

A field coil 82, for applying a magnetic field to a sample, has a diameter perpendicular to the longitudinal axis of the sapphire rod and is shown in FIGS. 1a and 1b, and may be wired to electronic measuring or controlling equipment as schematically shown in FIG. 6.

As discussed above, the design of window 28 FIG. 2 separates the SQUID chip 72 which is in vacuum space 18, from a sample 91 which is in air located outside of dewar 15. In order to obtain images of physical properties with spatial resolutions as fine as 50 µm, the separation of SQUID and sample should not be great and should be within 50 µm. To achieve a better spatial resolution, the SQUID must be smaller and closer to the sample. In order to accomplish this result, the window 28 must be thin and at the same time sufficiently broad to accommodate the SQUID chip, which must be positioned within a few µm of the window. The minimum width of the window depends on the width of the blunt end of the rod 56. In addition, window 28 should be stiff so as not to flex substantially under an atmosphere of pressure. That is, the window will flex less than its thicknes under one atmosphere; flexing of the window will necessarily increase separation between the SQUID and a flat sample. The window must also maintain a vacuum and it must be chemically inert, non-conducting and non-magnetic so that it does not interfere with the SQUID or react with a sample. Additionally, because it is very likely that the SQUID sample may accidentally contact the window, the window must be durable and must tolerate repeated contact with the sample. Finally, it has been noted that the window should preferably be transparent to the human eye (or to infrared or UV radiation which can be viewed with appropriate imaging systems) to help align the window, SQUID, and sample prior to a scan of the sample.

It has been found that transparent material having a Young's modulus of about 70 GPa to 670 GPa should be used. Preferably, this is a single-crystal sapphire (Al$_2$O$_3$) which is transparent and has a Young's modulus of about 50×10$^6$ psi.

Some materials which are suitable for windows include plastic, diamond, metallized films, MgO, SiN, LaAlO$_3$ and combinations thereof, as well as other materials. In addition, as discussed above, such materials should also be transparent. Window 28 is built by creating a window frame that includes drilling a conical hole in a 1.25 mm thick glass microscope slide 32 using a silicone-carbide tool. The diameter of this hole is 1 mm on the sample side and 3 mm in diameter on the SQUID side (see FIG. 2). The window frame may be made from any suitably stiff material including epoxy, glass, sapphire, diamond, etc.

Thereafter, a 25 µm-thick, 1 cm×1 cm single crystal of sapphire 30 is epoxied to the sample side of the glass slide 32 to form the 1 mm diameter, 25 µm-thick window 28 according to the following procedure. Having obtained this small window, it is waxed and adhered to a small glass holder. The window is then epoxied to the window frame 32 while it is still waxed to the holder. Once the epoxy hardens, the glass holder is removed by boiling the whole assembly in water to melt the wax. The total time in water should be kept to a minimum, because the water tends to temporarily soften the epoxy. The remaining side of the glass slide is epoxied to plastic flange 31 (see FIG. 2) which is then mounted to the dewar assembly through connecting structure 30 as shown in FIGS. 1b.

When setting up the microscope for imaging, the alignment of the window with respect to the SQUID is critical. Alignment is accomplished by using an optical microscope and a mirror to look directly through the thin sapphire window at the SQUID. The roughest approach is to simply move the window by adjusting nuts 64 or screws 63 until it touches the SQUID. With moderate relative humidity, it is possible to observe water condensing on the window when the SQUID is contacting the window. This is helpful for leveling the window with respect to the SQUID chip since the fog on the window indicates the location of contact between the SQUID and window.

It is also possible to detect thermal contact between the SQUID and the window by simply observing the SQUID voltage on an oscilloscope when oscillating flux is being applied to the SQUID. The degradation of the SQUID performance is quite sudden and significant when SQUID contact is made. Once the window is levelled with respect to the SQUID, the sample and scanning stage must be levelled with respect to the window. Levelling of the sample with respect to the plane of motion of the stage ensures that the separation between the sample and SQUID does not change during a scan. Levelling of the stage with respect to the window is necessary for achieving a small separation because of the relatively broad (1 cm) glass slide on which the sapphire window is mounted (see FIG. 2).

To obtain an image of the physical properties of a sample, individual raster scan lines are acquired by scanning the sample past the SQUID in the x direction while simultaneously recording the x coordinate and the relevant voltages (static field signal, rf-field signal, eddy-current signal, etc.) from the SQUID read-out electronics. This is repeated for the sequence of y values to construct the whole image.

The position of the stage is determined exclusively from the stepper-motor position. The control program of the computer 100 can read the stepper-motor position directly from the motor controller board which is mounted in computer 100. However, for proper synchronization of the x coordinate with the SQUID signal during a scan in the x direction, it is necessary to provide the data acquisition system with a voltage signal which is proportional to the instantaneous x position of the stage. This is accomplished using an external counter circuit which simply keeps track of the number of motor steps and adds this to, or subtracts this from, a position counter depending on the motor direction. The output from this counter is converted to a voltage level by using an integrated digital-to-analog converter. Hence, the counter simply functions as a position-to-voltage transducer.

Both the SQUID output and the position of the stage are read using an analog-to-digital converter and recorded using a personal computer. The personal computer also controls a scanning operation which generates the grid of position coordinates. Once a data set has been acquired using a control program, it is converted into an image. In its raw form, the image data consists of a set of "N" line scans (y-values) with the ith line containing a set of $M_i$ data points each having an x coordinate and one or more associated voltage values. To provide an image, this data is first spatially regularized, i.e., linearly interpolated onto a rectangular spaced grid. Then an image rendering program is used to assign a color, or a level of gray to each grid point.

The sample stage 90 can be moved by manually operating drive screws and a very simple data acquisition program can be used to record the position of the sample stage using potentiometers attached to the x and y drive screws on the microscope while simultaneously recording the SQUID output. A second program to convert the stream of positions and values into a set of values on a rectangular grid can be used and finally each value in the grid can be assigned a color and an image can be displayed.

This procedure, especially scanning the sample manually, is quite time consuming and monotonous. Accordingly, a control program has been written and is used to operate the stage, record the SQUID output and then display an image.

In essence two stepper motors are operated using a controller board which is physically mounted in computer 100 along with a multifunction input-output (IO) board which is primarily used as an analog-to-digital converter (ADC) for reading the output from the SQUID electronics. Hence, both motion control and data acquisition are accomplished using a single personal computer.

Since the SQUID is basically a point-like probe, it must be scanned in a raster pattern to form an image. The raster pattern consists of a series of lines in the x direction at different values of y, stacked together to form an image.

Figure 7:
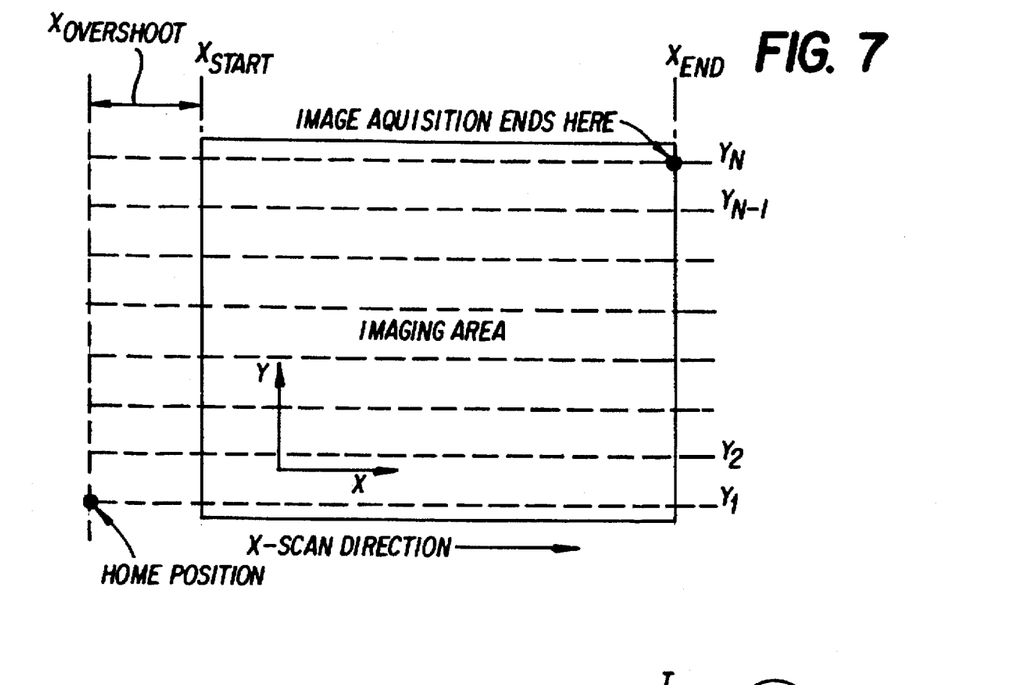
FIG. 7 is a diagram showing the scanning pattern used by the control program. Dashed lines show the paths of the SQUID (relative to the sample) during a scan.

To take an image with the microscope, the computer first positions the sensor 70 to the "home" position $x=x_{start}-x_{overshoot}$, $y=y_1$, where $x_{start}$ corresponds to the left edge of the image area, $y_1$ is y coordinate of the first scan-line and $x_{overshoot}$ is the hysteresis length in the x scanner (see FIG. 7). It is necessary to overshoot the left edge of the image area by $x_{overshoot}$ prior to scanning each line to eliminate the backlash in the scanning mechanism. Next, the x position of the SQUID is increased at constant velocity (to the right) until $x=x_{start}$ at which point the computer begins recording the x position and the SQUID signal $V_{out}$. If needed, additional channels of data, up to the limits of the IO-board, can be acquired at the same time. The data is continuously sampled until $x=x_{end}$ at which point the data acquisition for this scan-line ends and the single scan-line is written to the data file. At this point the x position of the SQUID is "rewound" to $x=x_{start}-x_{overshoot}$ and the y- position advanced to $y=y_2$ in preparation for acquiring the second scan-line. This procedure is repeated until all N scan-lines are acquired and written to disk.

Once all N scan-lines have been written to the data file, they must be converted into an image. To accomplish this, the individual scan-lines must be spatially projected onto a rectangular grid. While the raster lines at $y_1, y_2 \ldots, y_n$ are evenly spaced in the y direction, the data points in the x direction are not regularly spaced with respect to each other. That is, while the data points in any given scan-line may be uniformly spaced, they may be shifted with respect to an adjacent scan-line. Hence the program must line up the x values in all the scan-lines by defining an evenly spaced grid in the x direction and then computing $V_{out}$ at each of these points by linearly interpolating the data from the raw scans.

Once this is done, all that is left to do is to convert the resulting uniform grid of values into an image by assigning colors or shades of gray to each value in the grid. Various commercially available computer programs can be used to do this. One such program is called "Transform," produced by Spyglass, Inc. in Champaign, Ill.

An important capability of this software is the ability to select an arbitrary "scan" variable and "raster" variable. While in the description of the scanning procedure above, x was chosen as the "scan" variable and y as the "raster" variable, with this more generalized approach to selecting the independent variables, it is equally acceptable to scan the y coordinate and treat x as the raster variable. Furthermore, other parameters for the scan coordinate could be chosen. For instance, the computer can also control the voltage output from a digital-to-analog converter in the IO-board which can subsequently be used to set the frequency of an rf source used for, say, driving the sample. Hence, it is sufficient to produce an image containing frequency versus x by choosing the frequency of the rf source as the "scan" variable and the position of the x motor as the raster variable. Obviously many other combinations are possible as well.

Since the "scan" and "raster" variables can be chosen independently, it is naturally possible to use the same program with different microscopes and sensors. This is done by simply choosing the scan and raster variables for the appropriate microscope.

Figure 8:
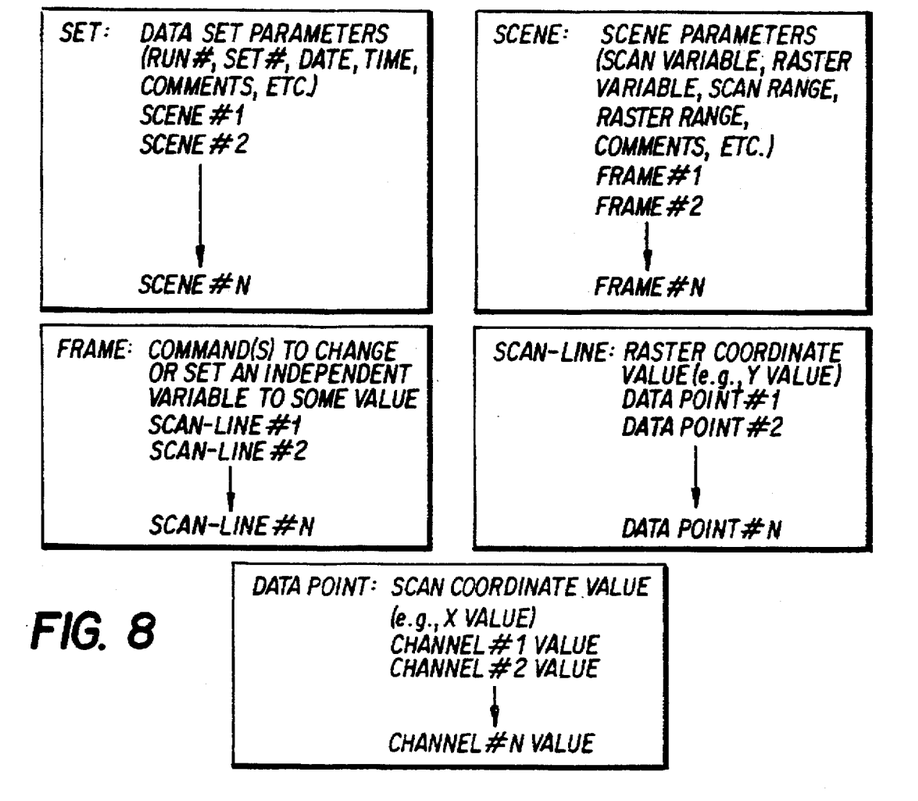
FIG. 8 is a hierarchical format for data set.

Often it is useful to program a series of image acquisitions to occur under program control. For instance, suppose one would like to take an image, change a parameter, take another image, change a parameter again and continue, thus producing a sequence of images suitable for a movie. To address this, the program has a variety of programming features which allow the acquisition of images without operator intervention. This is accomplished by organizing the multiple images into a single "set" which consists of an arbitrary number of "scenes." Each "scene" can contain an arbitrary number of "frames." And each frame represents a single image, composed of multiple scan-lines of data points (see FIG. 8). The parameters for a particular "scene" determine which variable is used for the "raster" variable and which for the "scan" variable. Also the "scene" determines the values for $x_{start}, x_{end}, y_1, y_2, \ldots, y_N$, scan speeds, data sampling rates, and most other imaging parameters. So, if one wants to acquire a number of virtually identical images with only, say, a single parameter change between images, a single "scene" will be used with multiple frames. The "set" is simply a sequential ordering of any number of different "scenes" to be acquired. With this structure, it is possible to program virtually any combination.

An important part of data acquisition is recording the operating parameters of the system when the data is taken. In order to assure reproducibility, all relevant parameters must be saved. With this program, this is done by using a "document" type interface for data sets. After a data set is acquired it is held in a temporary buffer area. The "set" can then be save along with all the relevant parameters in the data acquisition program which were in effect when the data was acquired. At a later time, this data set can be opened and read back into the program thus returning all the parameters in the program including the buffer file to the state it was in when the data was originally taken. Hence, each of these saved data sets represents a snap-shot of the state of the program after imaging and hence contains a complete record of the imaging parameters. This saves a great deal of time usually spent writing down parameter values in a notebook.

To demonstrate the ability of the microscope to image static magnetic fields, a ferromagnetic sample and a sample carrying a dc current were imaged. In each case the microscope is operated in a flux-locked loop.

Figure 9A:
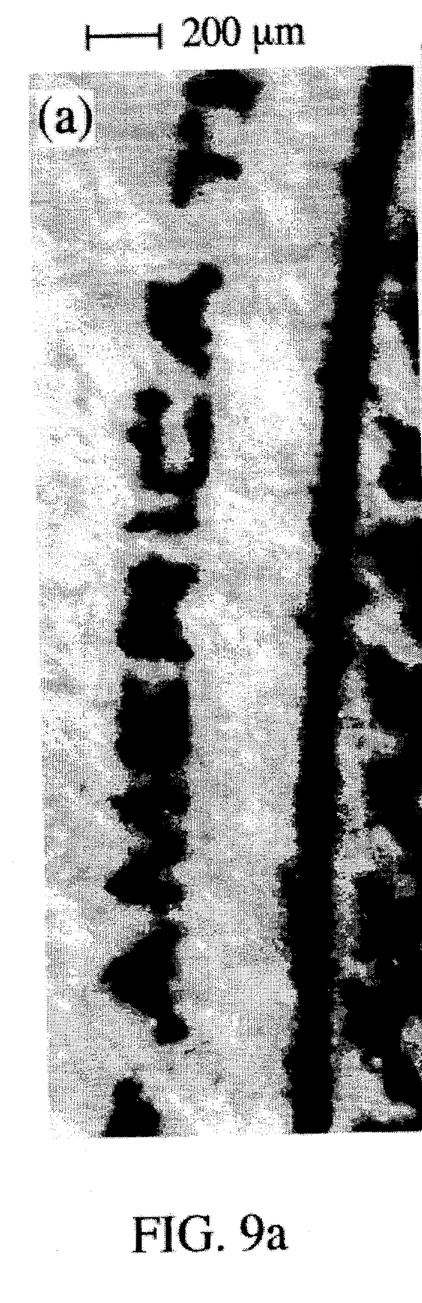
FIG. 9a is a photomicroprint of the fine ink pattern around the portrait on a $100 bill.
Figure 9B:
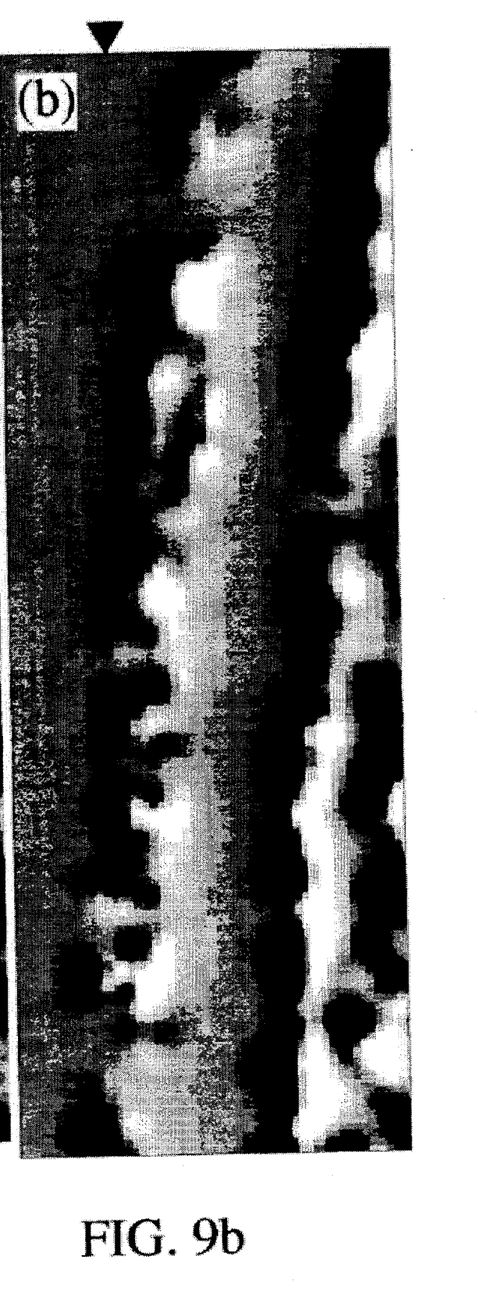
FIG. 9b shows the magnetic-field image with fields ranging from 500nT (black) to 500nT (white).

FIG. 9(a) shows a photographic image of the fine printing (microprint) around Benjamin Franklin's portrait on a $100 U.S. Federal Reserve Note. FIG. 9(b) shows the corresponding static magnetic field image of the same region. The ink in this sample is ferromagnetic and hence produces a substantial magnetic signal. To achieve the best spatial resolution, the sample was scanned in direct contact with the sapphire window. This is possible because of the flatness of the sample and the hardness of the window material. The magnetic fields in the image range from −500 nT (black) to 500 nT (white). These field variations are about 1000 times larger than the noise threshold of the image and so this sample does not necessarily demonstrate the field sensitivity of the instrument. However, the small feature size in the sample does provide a good test of the spatial resolution.

Figure 10:
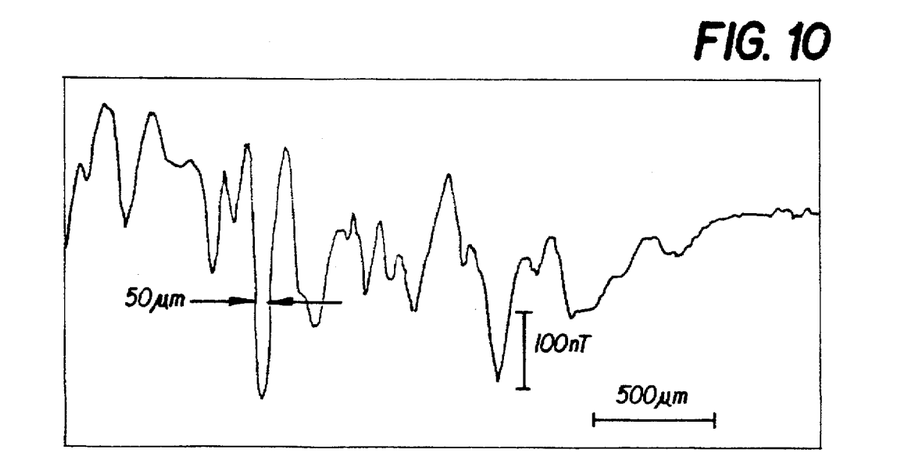
FIG. 10 is a vertical slice through the magnetic image shown in FIG. 9B indicating a spatial resolution of 50 μm.

The spatial resolution of the instrument can be deduced from FIG. 10 which shows a vertical slice (from bottom to top) through the magnetic image in FIG. 9(b) along the line indicated by the triangle. By measuring the full width at half maximum of the sharpest peak in this and similar slices, a spatial resolution of about 50 µm is deduced. The data indicates that the separation between the SQUID and the surface of the sample should be less than 50 µm. This is about a factor of 30 times smaller than any other previously published SQUID-based system which can image room-temperature samples in air.

Figure 11:
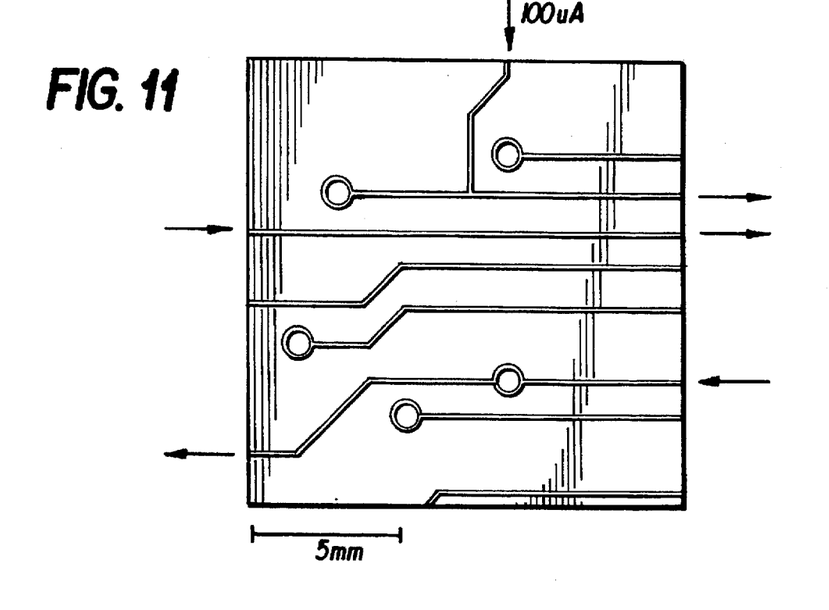
FIG. 11 is a photograph of printed circuit board with arrows indicating current flow (100 μA) in wires.

In an environment where the microscope would be used for nondestructive testing applications, the quasistatic fields are more likely to be produced by flowing currents. FIG. 11 is a photograph of a small portion of a printed circuit board showing a number of copper interconnects and solder points. A current of 100 µA is flowing in the wires as indicated by the arrows.

Figure 12:
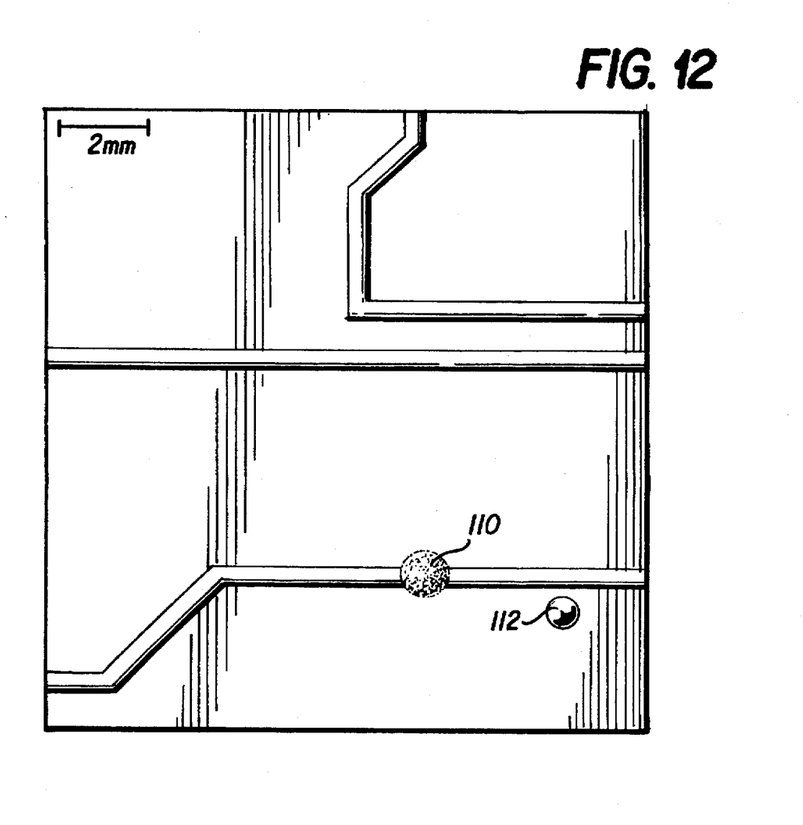
FIG. 12 shows the static magnetic field image of current flow in printed circuit board of FIG. 11.

FIG. 12 is a magnetic image of this sample obtained by scanning at a separation of about 200 µm between the window and the surface of the circuit board. While the spatial features in this image are not difficult to resolve, the fields produced by the currents, which range over about 80 nT, are considerably smaller than before. Hence, it was necessary to first obtain a background image without the sample, then subtract this from the raw magnetic image of the circuit board.

The image clearly indicates which conductors are carrying a current and which are not. Also, by application of the right-hand rule, it is possible to determine the direction of current flow. Furthermore, magnitudes of the currents can also be extracted in principle by modeling the field produced by a current I in one of the interconnects. Because the data used to generate the image is quantitative, a fitting algorithm could be utilized to find I. Even in the case where the density of interconnects causes significant overlap of the fields in the image, more advanced deconvolution algorithms can be used to extract the directions and magnitudes of the currents.

Note that circuit boards like the one shown inevitably contain magnetic contamination in the form of small particles of steel, resulting from handling or machining. One such particle 110 is seen in the lower right corner of FIG. 12 where it produces a characteristic dipole signature. However, even if a contaminant 110 does not have a strong magnetic signature, it may also be detectable when it is located in a conducting pathway where it could degrade circuit performance. For example, note the distinctive effect of the current flowing across the solder point 112 near the bottom of FIG. 12. The perturbation of the current by the hole alters the field as is easily seen in the image. While the hole is rather larger in this case, the clarity of the image suggests that much smaller nonuniformities in current flow could be detected. This technique could ultimately be use to detect small voids or particulate contamination in critical conducting pathways, possibly beneath the surface, which would otherwise not be apparent until after the circuit failed.

In some cases, it is not possible or practical to directly inject currents into a sample for imaging. However, by applying an alternating magnetic field to the sample, alternating eddy currents can be induced in the sample for probing defects.

To further illustrate the capabilities of the microscope, eddy-current images of a variety of metallic samples, including an aluminum "lap-joint" assembly as used in aircraft fuselage construction were tested. A lap-joint is where two sheets of aluminum skin are joined together and riveted to a support strut. The detection of defects in lap-joints is the goal of some of the existing eddy-current NDE efforts.

A ¼-scale model of an aluminum (resistivity $\rho \approx 0.6\ \mu\Omega$ cm at 77 K) lap-joint was constructed. In the scale model, an upper and lower sheet of 0.2 mm-thick aluminum are jointed to a 0.8 mm-thick support strut by means of 1.6 mm-diameter rivets with 2.5 mm-diameter heads. The rivet heads are made flush with the sample surface as is done in real aircraft construction. A crack 114 which extends to a radius of about 3 mm from the center rivet was placed in the bottom layer of the skin so that it is not visible from either the top or bottom of the assembled sample. The crack was formed by shearing the metal and then flattening it again before riveting the sample together; this leaves a very tight crack with no gap.

Figure 13:
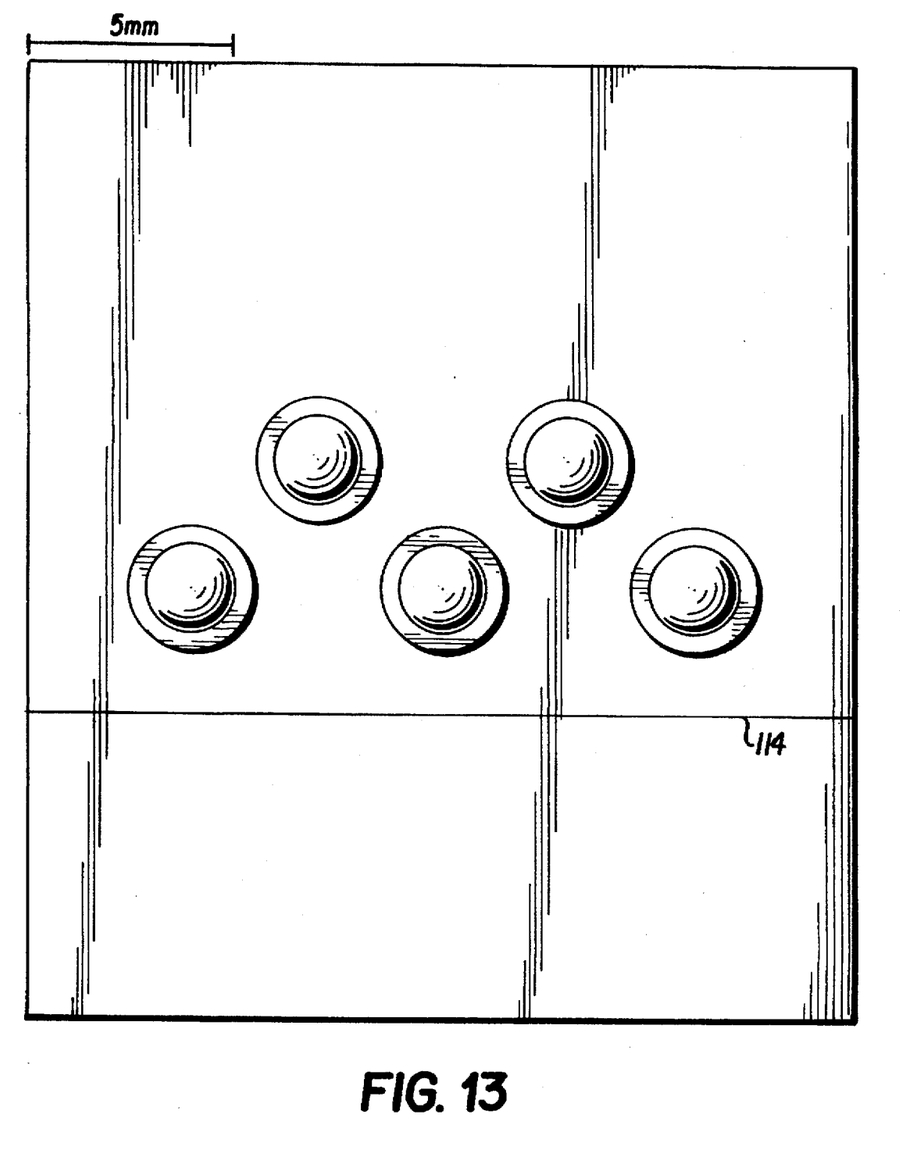
FIG. 13 shows a 49 KHz eddy-current image of a lap-joint sample.
Figure 14A:
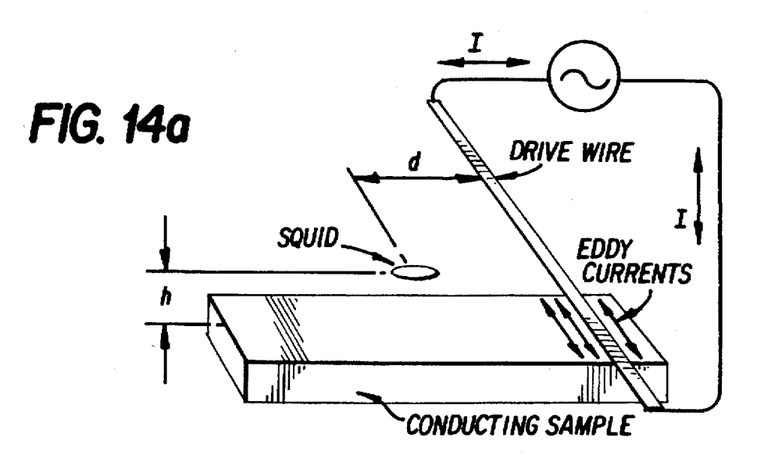
FIG. 14a shows a drive coil arrangement used for the eddy-current detection of subsurface cracks in conductors.
Figure 14B:
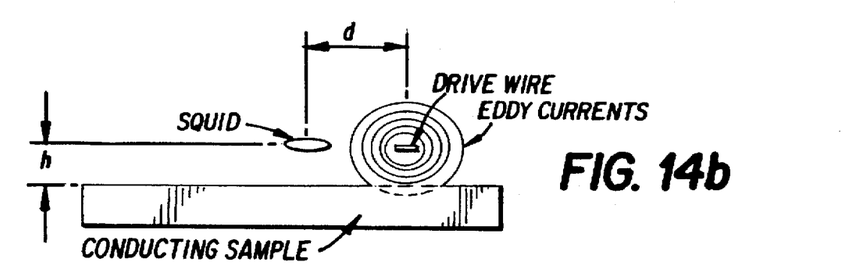

FIG. 13 shows a 49 kHz eddy-current image of this sample. To obtain the best results, a linear drive wire oriented in the plane of the sample to induce eddy currents, as shown in FIGS. 14a and 14b, was used. This induces eddy currents which are strongly perturbed by the geometry of the crack. In addition to the five rivets, the buried crack which extends diagonally from the center rivet is clearly resolved in this image. Other structure is also visible in this image. For example, the image indicates the presence of the thicker support strut in the region beneath the rivets.

Since many electrical circuits operate at high frequencies, another potentially important imaging technique involves imaging the rf fields produced by rf currents flowing in a sample. For example, silicon-based high-frequency circuits are not designed to function at 77 K. The ability to examine room-temperature samples makes it possible to apply the rf imaging capabilities of a scanning SQUID microscope to this class of samples.

Figure 16:
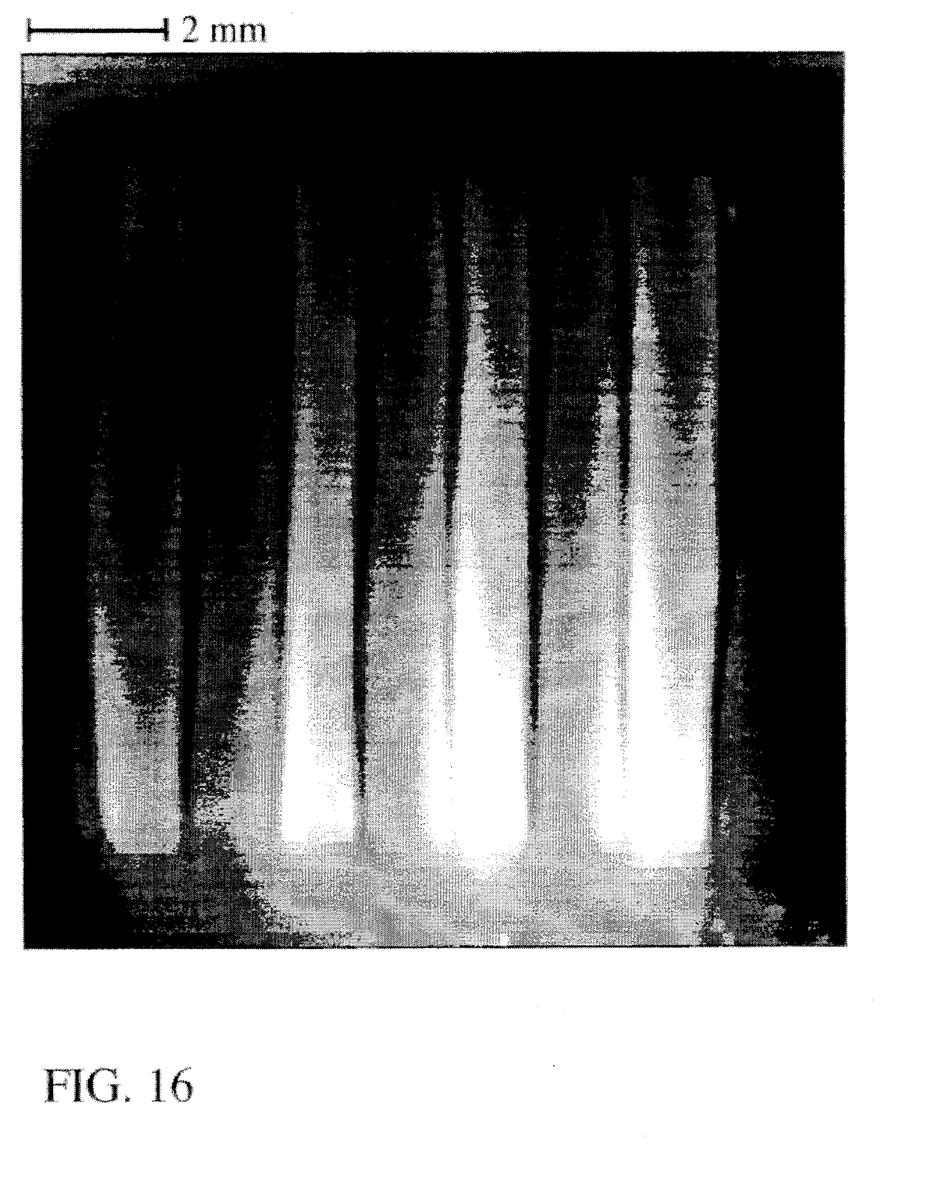
FIG. 16 shows the radio frequency image of a 400 MHz current flowing in the wire meander of FIG. 15.

To test the microscope's rf-field imaging capabilities on a room-temperature sample, the rf fields in the vicinity of the wire-meander sample shown in FIG. 15 were imaged. A 400 MHz rf current is driven in the wire using an rf voltage source. FIG. 16 shows the rf image of the 400 MHz fields produced over the surface of this sample. The brightest regions correspond to an rf-field magnitude of about 200 nT. The darkest regions, including the lines corresponding to locations of the wire, are where the z component of the field is zero. This image emphasizes the point that, when configured for imaging rf fields, the microscope is only sensitive to field magnitude and not field amplitude.

In previous work, it was found that the maximum frequency at which this technique functioned properly was about 150 MHz. Beyond this, cavity mode resonances in the SQUID substrate produced artifacts in the images and effectively degraded the spatial resolution. Clearly, FIG. 16 shows that the bandwidth of the room-temperature microscope is higher for this type of imaging. The reason for this improvement is that the substrate size is a factor of 4 smaller in the room-temperature system. By using a smaller SQUID substrate, the frequency at which the lowest cavity mode will oscillate is increased proportionately, along with the frequency at which the image deteriorates.

While the above images were made using a SQUID, many other types of cryogenic sensors could be used. The advantage of using other types of cryogenic sensors is that, when used in the apparatus, they will allow the sensitive microscopic imaging of other physical properties which the SQUID is not sensitive to.

Such cryogenic sensors include: bolometers for imaging microwave, optical, UV, and infrared radiation; multiple SQUIDS for more rapidly acquiring images; Hall probes for measuring magnetic fields from samples; simple junction superconducting devices for measuring microwave and far-infrared radiation; multiple junction superconducting devices for imaging magnetic fields or microwave and for infrared radiation; Giant Magnetoresistance or Collosal Magneto resistance devices for imaging magnetic fields; single electron transistor devices or Coulomb blockade devices for imaging electric fields and charges and dielectronics; photocathod and photoresistive devices for imaging optical, UV and far infrared radiation, cryogenic field effect devices (FET's) for imaging electric fields, and 2-D electron gas devices ((2-DEG) for imaging electric fields and magnetic fields.

While the invention has been described with reference to specific drawings and embodiments, modifications and variations thereof may be made without departing from the scope of the invention which is defined in the following claims.

What is claimed is:

1. An apparatus for enabling a cryogenic measuring device to generate microscopic spatially resolved images of physical properties of a sample, comprising a housing comprised of a first section for holding a cryogen or a cryogenic cooling apparatus and a second section enclosing a vacuum space, at least a portion of the second section is a thin transparent window separating the vacuum space from ambient atmosphere;

a cryogenic measuring device for measuring the physical properties of a sample to obtain resolved images thereof, said cryogenic device is located within the housing having a measuring end disposed adjacent the thin transparent window of the housing for scanning said sample, said sample being located outside of the housing; alignment of said sample measuring device and thin transparent window of the housing facilitated by the transparency of the window;

means for adjusting the distance between the cryogenic measuring device and the window and means for adjusting the distance between the sample and the cryogenic measuring device to allow the cryogenic sensor to be within microns of the sample; and means for converting an output from the cryogenic measuring device measuring the sample to images from physical properties of said sample.

2. The apparatus of claim 1 including means for recording the output from the cryogenic measuring device.

3. The apparatus of claim 1 wherein the window is microscopically thin and has a stiffness such that at 1 atmosphere it will flex less than its thickness.

4. The apparatus of claim 1 wherein the cryogenic measuring device comprises a thermally conducting substrate and at least a portion of the thermally conducting substrate is in heat exchange contact with the cryogen or cryogenic cooling apparatus and at least a second portion of the thermally conducting substrate has affixed thereto a cryogenic sensor defining the measuring end of the cryogenic measuring device.

5. The apparatus of claim 1 wherein the thin, transparent window is selected from plastic, sapphire, diamond, metallized films, MgO, SiN, and $LaAlO_3$.

6. The apparatus of claim 4 wherein the thermally conducting substrate is rod shaped, wherein a first end thereof has a blunt-point shape and mounted to the blunt-point shape is the cryogenic sensor.

7. The apparatus of claim 1 measuring device wherein the cryogenic comprises a member selected from the group consisting of single SQUIDS, multiple SQUIDS, Hall probes, single junction superconducting devices, multiple junction superconducting devices, Giant Magneto-Resistance (GMR) Effect devices, Collosal Magneto-Resistance (CMR) Effect devices, single electron transistors, coulomb blockade devices, bolometers, photocathodes, photoresistive devices, cryogenic field effect devices, and 2-D electron gas devices.

8. The apparatus of claim 5 where the cryogenic measuring device is a SQUID sensor.

9. The apparatus of claim 8 wherein the SQUID sensor is made from $YBA_2CU_3O_2$.

10. The apparatus of claim 1 further comprising a holder for holding the sample in a position in the front of the window and outside of the housing, a means for moving the holder, and means for controlling movement of the means for moving the holder.

11. The apparatus of claim 10 wherein said holder is a stage and said means for moving the holder includes at least one motor.

12. The apparatus according to claim 11 wherein said stage has a composition such that the operation of the stage does not adversely affect said sensor or sensitivity to said sample.

13. The apparatus of claim 11 wherein the stage is an x-y-z stage.

14. The apparatus according to claim 1 further comprising a computer for controlling the sample position, and for monitoring the sensor output.

15. The apparatus according to claim 12 where the apparatus is composed of non-magnetic and non-conducting materials.

16. An apparatus according to claim 1 where the window is thinner than 0.1 mm and consists essentially of sapphire.

17. A method for imaging microwave, optical, UV or infrared radiation of a sample, comprising:

scanning the sample with a cryogenic measuring device positioned within microns of the sample and capable of detecting microwave, optical, UV and infrared radiation of the sample, the cryogenic measuring device located in a housing comprised of a first section for holding a cryogen or a cryogenic cooling apparatus and a second section enclosing a vacuum space, at least a portion of the second section is a thin transparent window separating the vacuum space from ambient atmosphere; the cryogenic measuring device having a detecting end disposed adjacent the thin transparent window of the housing for scanning the sample located outside of the housing;

detecting the microwave, optical, UV or infrared radiation of the sample with the detecting end of the cryogenic measuring device, said cryogenic measuring device generating an output; and converting the output to obtain images from the microwave, optical, UV or infrared radiation properties of said sample.

18. A method according to claim 17 wherein the cryogenic measuring device comprises a bolometer.

19. A method for obtaining images of magnetic fields from a sample, comprising scanning the sample with a cryogenic measuring device, the cryogenic measuring device located in an apparatus comprising a housing comprised of a first section for holding a cryogen or a cryogenic cooling apparatus and a second section enclosing a vacuum space, at least a portion of the second section is a thin transparent window separating the vacuum space from ambient atmosphere; the cryogenic measuring device within the housing having a measuring end disposed adjacent the thin transparent window of the housing for scanning the sample through the thin transparent window, said sample located outside of the housing;

detecting the magnetic field of the sample to spatial resolutions of 50 µm with the measuring end of the cryogenic measuring device, said cryogenic measuring device generating an output; and converting the output to obtain images from the magnetic field of said sample.

20. The method of claim 19 wherein the cryogenic measuring device comprises a SQUID, Hall probe, GMR or CMR device.

21. A method for measuring electric fields from a sample, comprising scanning the sample with a cryogenic measuring device, the cryogenic measuring device located in an apparatus comprising a housing comprised of a first section for holding a cryogen or a cryogenic cooling apparatus and a second section enclosing a vacuum space, at least a portion of the second section is a thin transparent window separating the vacuum space from ambient atmosphere; the cryogenic measuring device within the housing having a measuring end disposed adjacent the thin transparent widow of the housing for scanning through the thin transparent window, a sample located outside of the housing; and detecting the electrical field of the sample to spatial resolutions of 50 µm with the measuring end of the cryogenic measuring device, said cryogenic measuring device generating an output; and converting the output to obtain images of the sample from the electrical field.

22. An apparatus for enabling a cryogenic measuring device to generate microscopic spatially resolved images of physical properties of a sample, comprising a housing comprised of a first section for holding a cryogen or a cryogenic cooling apparatus and a second section enclosing a vacuum space, at least a portion of the second section is a thin transparent window separating the vacuum space from ambient atmosphere;

a cryogenic measuring device for measuring the physical properties of a sample to obtain resolved images thereof, said cryogenic measuring device is located within the housing having a measuring end disposed adjacent the transparent window for scanning a sample, said sample is located outside of the housing;

means for moving the transparent window and the cryogenic measuring device relative to one another so that the sample and the cryogenic measuring device are positioned within microns of one another;

means for delivering a cryogen from the first section of the housing to a thermally conducting substrate in heat exchange with the cryogenic measuring device; and means for converting an output from the cryogenic measuring device measuring the sample to obtain images of physical properties of said sample.

23. The apparatus of claim 22 wherein means for delivering a cryogen from the first section of said housing to the substrate in heat exchange with the cryogenic measuring device comprises a bellowed conduit having a first end in open communication with the cryogen and a second end for delivering cryogen to the substrate.

24. The apparatus of claim 23 wherein said substrate comprises sapphire.

25. An apparatus for enabling a cryogenic measuring device to generate microscopic spatially resolved images of physical properties of a sample, the apparatus comprising:

a housing comprising a first section for holding a cryogen or a cryogenic cooling apparatus and a second section enclosing a vacuum space, at least a portion of the second section being a thin transparent window separating the vacuum space from ambient atmosphere;

a cryogenic measuring device for measuring the physical properties of the sample and for producing an output representative of the physical properties to obtain resolved images of the sample, the cryogenic device being located in the housing and having a measuring end disposed adjacent the thin transparent window of the housing for scanning the sample, the sample being located outside of the housing, alignment of the cryogenic measuring device and the thin transparent window of the housing being facilitated by a transparency of the window;

sample holding means for holding the sample outside of the housing;

moving means for causing relative movement between the cryogenic measuring device and the sample holding means which allow the cryogenic sensor to be within microns of the sample and so that the cryogenic measuring device and the sample holding means successively attain a plurality of relative positions;

position detecting means for detecting the plurality of relative positions and for outputting a position signal representing the plurality of relative positions; and imaging means, receiving the position signal and the output from the cryogenic measuring device at each of the plurality of relative positions, for deriving the resolved images of the sample from the position signal and the output.

26. The apparatus of claim 25, wherein:

the sample holding means is movable in at least x and y directions relative to the cryogenic measuring device; and the moving means comprises means for moving the sample holding means in at least the x and y directions relative to the cryogenic measuring device to achieve a raster scan of the sample.

27. The apparatus of claim 26 wherein, the sample holding means comprises a sample stage movable in at least the x and y directions; and the moving means comprises stepper motors for moving the sample stage in at least the x and y directions.

28. An apparatus for enabling a cryogenic measuring device to generate microscopic spatially resolved images of physical properties of a sample, comprising a housing comprised of a first section for holding a cryogen or a cryogenic cooling apparatus and a second section enclosing a vacuum space, the second section comprises a plate defining an opening, a window support spaced apart from said plate, means for connecting the plate to the window support enabling movement of the window support relative to the plate and a thin transparent window positioned on the window support, said window, window support, means for connecting, and plate defining structure enclosing the vacuum space;

a cryogenic measuring device for measuring the physical properties of a sample to obtain resolved images thereof, said cryogenic device is located within the second section of the housing having a measuring end disposed adjacent the thin transparent window for scanning said sample, said sample being located outside of the housing; alignment of said sample measuring device and thin transparent window of the housing facilitated by the transparency of the window;

threaded means for adjusting the distance between the cryogenic measuring device and the window, and stage means supporting the sample for adjusting the distance between the sample and the window, said threaded means and said stage means allowing the cryogenic sensor to be within microns of the sample; and means for converting an output from the cryogenic measuring device measuring the sample to images from physical properties of said sample.

29. The device of claim 28 wherein said means for connecting comprises a bellows which also defines a thermal cooling path.

30. The device of claim 28 wherein the window is thinner than 0.1 mm and comprises sapphire.

31. The device of claim 30 wherein the cryogenic measuring device is a SQUID.

* * * * *